(12) United States Patent
Barrett et al.

(10) Patent No.: US 10,245,334 B2
(45) Date of Patent: Apr. 2, 2019

(54) REFRACTION TECHNOLOGY SYSTEM

(71) Applicants: Richard J. Barrett, Rothschild, WI (US); Michael Carstensen, Weston, WI (US)

(72) Inventors: Richard J. Barrett, Rothschild, WI (US); Michael Carstensen, Weston, WI (US)

(73) Assignees: Richard J. Barrett, Rothschild, WI (US); Michael Carstensen, Weston, WI (US)

( * ) Notice: Subject to any disclaimer, the term of this patent is extended or adjusted under 35 U.S.C. 154(b) by 197 days.

(21) Appl. No.: 15/225,949

(22) Filed: Aug. 2, 2016

(65) Prior Publication Data
US 2017/0035921 A1    Feb. 9, 2017

Related U.S. Application Data

(60) Provisional application No. 62/201,236, filed on Aug. 5, 2015.

(51) Int. Cl.
| | |
|---|---|
| *A61L 9/00* | (2006.01) |
| *A61L 2/00* | (2006.01) |
| *A62B 7/08* | (2006.01) |
| *A61L 2/02* | (2006.01) |
| *C02F 1/461* | (2006.01) |
| *A61L 2/03* | (2006.01) |
| *C02F 1/46* | (2006.01) |
| *C02F 1/32* | (2006.01) |

(52) U.S. Cl.
CPC ............ *A61L 2/035* (2013.01); *C02F 1/4602* (2013.01); *A61L 2202/11* (2013.01); *A61L 2202/17* (2013.01); *C02F 1/325* (2013.01); *C02F 2201/46115* (2013.01); *C02F 2201/46125* (2013.01); *C02F 2209/04* (2013.01); *C02F 2301/08* (2013.01); *C02F 2303/04* (2013.01); *C02F 2303/14* (2013.01); *C02F 2303/20* (2013.01); *C02F 2305/023* (2013.01)

(58) Field of Classification Search
CPC ........................................................ C25B 1/26
USPC .... 422/186.04, 1, 4, 22, 121–122, 305–306; 205/701, 742; 204/263, 265, 272
See application file for complete search history.

(56) References Cited

U.S. PATENT DOCUMENTS

| | | | |
|---|---|---|---|
| 8,110,089 B2 | 2/2012 | Mortensen | |
| 2005/0142157 A1* | 6/2005 | Alimi | ..................... A01N 59/00 424/405 |
| 2013/0146473 A1* | 6/2013 | Lambert | ................... C25B 1/26 205/510 |

\* cited by examiner

*Primary Examiner* — Monzer R Chorbaji

(57) ABSTRACT

A system and method for modifying monoatomic oxygen levels in an initial fluid, for applications. The system and method produces both positive and negative oxygen modified fluid that retains oxygen levels for long durations as measured by oxygen reduction potential (ORP). An incoming fluid is split between a positive chamber defined by a cathode and a porous divider and a negative chamber defined by the porous divider and an anode. The relative charge over the porous divider produces fluid with elevated ORP from the positive chamber and fluid with lowered ORP from the negative chamber. A method of killing bacteria includes contacting the bacteria with negative ORP fluid produced in the system and method to the bacteria.

18 Claims, 5 Drawing Sheets

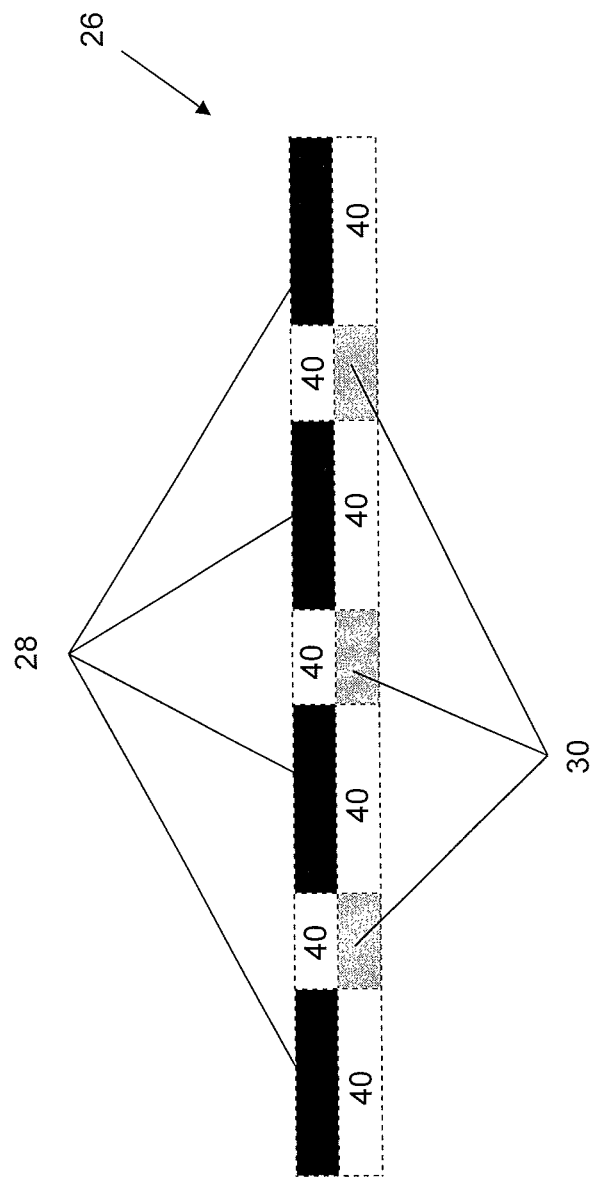

Figures 4A-4E
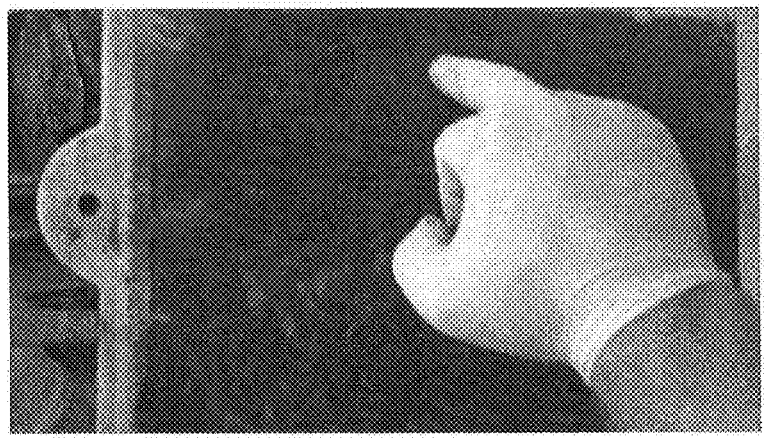
Figure 4A
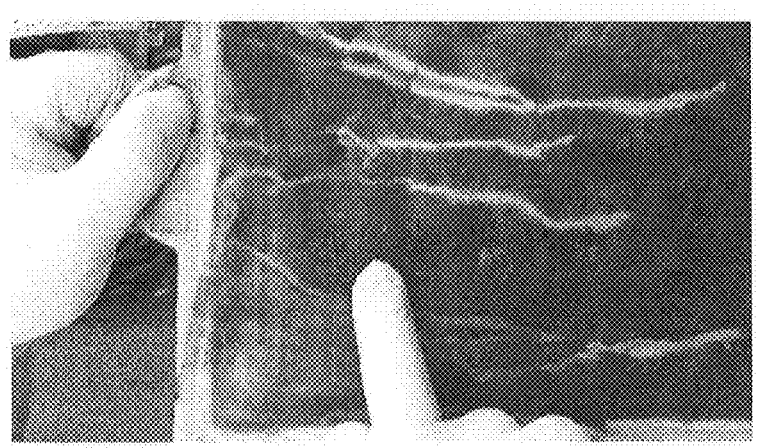
Figure 4B

REFRACTION TECHNOLOGY SYSTEM

CROSS-REFERENCE TO RELATED APPLICATION

This application claims priority from U.S. Provisional Patent Application No. 62/201,236 filed Aug. 5, 2015, the entire content of which is incorporated herein by reference.

BACKGROUND OF THE DISCLOSURE

The disclosure relates to fluid modification. More particularly, the disclosure relates to a refraction system and method for modifying fluid to produce high (i.e., "positive") and/or low (i.e., "negative") oxygen content fluid.

A complete understanding of the disclosed system may be obtained by reference to the accompanying drawings, when considered in conjunction with the subsequent, detailed description, in which the technology was primarily designed for the flushing and rinse cleaning of the clogged and embedded materials captured on filtering screens, hard surfaces, of all materials or similar applications, as shown in the photographs of FIG. 4. The disclosed refraction technology oxidation reduction potential, (ORP) modification has proven efficient at producing a large volume of electronically modified ORP fluid, which was proven to be particularly useful in cleaning and disinfecting bacteria infected screens, eliminating the use of dangerous chemicals and extending the life of the equipment in this operation example.

Fluids having an elevated positive ORP (i.e., higher concentration of monoatomic oxygen) increase oxidation, and thus can provide pathogen killing properties. For example, chlorine has a high ORP value and is commonly used as a disinfectant additive. Conversely, it is known that the ORP of healthy humans is negative and consumption of fluids with positive or even neutral ORP values consumes energy from cell membranes to reduce the ORP to the body's natural level. Accordingly, studies indicate that consuming fluids with negative ORP value (i.e., reducing agent) helps individuals maintain natural body chemistry and accordingly carry many health benefits.

Disclosed herein is a system and method for non-chemically creating modified positive and negative charged ORP fluid streams. These modified fluid output streams carrying electrically modified ORP levels ranging, for example, from approximately +1200 ORP to approximately −700 ORP (specific range is adjustable and non-limiting).

It is known that conventional ORP modified fluids will naturally return toward a neutral ORP level over time, oftentimes very rapidly. As a result, common ORP modified products need to be applied or consumed in a timely manner to be most effective for the desired use and effect. In addition to modifying ORP levels in incoming fluids without requiring chemical additives, the disclosed system and method has proven to yield modified fluids that maintain modified ORP levels for longer durations than known chemical-based ORP modification methods.

SUMMARY

There is a need for a refraction technology oxygen modification system and method for efficiently producing modified ORP fluids at adjustable levels of charge on a large scale without introduction of chemicals. Moreover, there is a need for a system and method for producing modified ORP fluid that maintains its altered ORP level for extended durations.

The disclosed refraction system and method efficiently provides two adjacent flow paths through separate chambers for fluid treatment—one carrying a positive charge that yields an output flow of positive ORP fluid; and the other carrying a negative charge that yields an output flow of negative ORP fluid. The positive and negative ORP fluids are produced from the system simultaneously. Tests have shown that positive ORP fluid modified via the disclosed refraction system and method have proven to provide a more efficient and chemical-free cleansing and rinsing technique for eliminating bacteria without the use of dangerous chemicals (such as concentrated hydrochloric acid). In a test for cleaning and disinfecting a filter screen at a sewage treatment plant, positive ORP modified fluid produced by the disclosed system and method showed significantly superior results compared to presently used materials and processes which require harsh and highly concentrated chemicals.

BRIEF DESCRIPTION OF THE DRAWINGS

Aspects of the preferred embodiment will be described in reference to the Drawings, where like numerals reflect like elements:

FIG. 3 is an end view of an end cap employed within the disclosed refraction oxygen modification system; and FIGS. 4A-4E show a series of photographs depicting treatment of a contaminated filtration screen using the negatively charged fluid modified within the refraction oxygen modification system of FIGS. 1 and 2.

DETAILED DESCRIPTION

Figure 1:
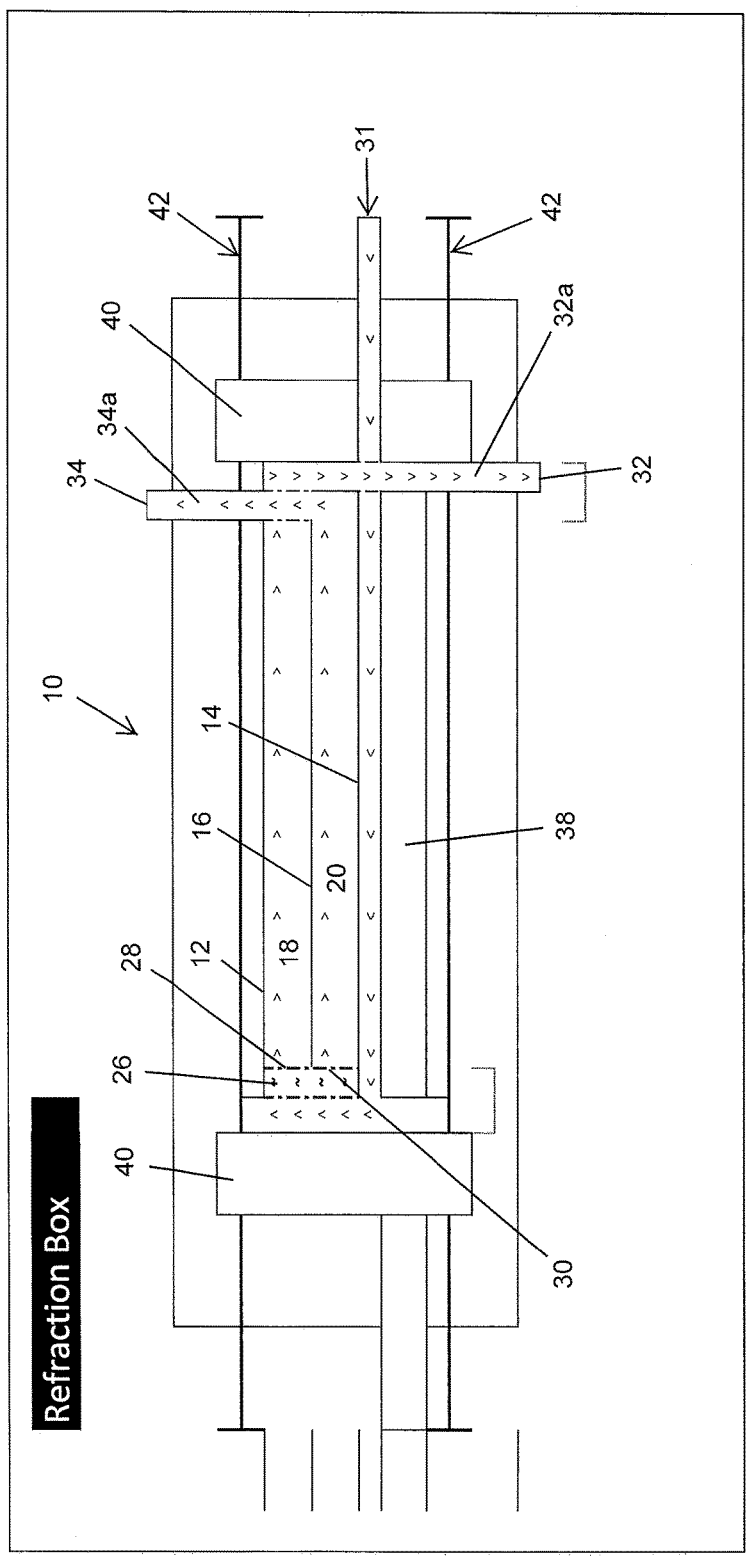
FIG. 1 is a side schematic of an embodiment of a refraction oxygen modification system in accordance with the disclosure.

A schematic of a refraction technology oxygen modification system is designated as reference numeral 10 in FIG. 1. Multiple modified fluid streams are prepared by providing a primary stream of incoming fluid having an initial ORP value to the system 10 via the inlet 31. The incoming fluid typically ranges from tap water to waste water of average hardness and mineral content, though the disclosed embodiment is not so limited. The refraction technology oxygen modification system 10 can be adjusted in real time during operation to provide a specific range of desired flow rates. A preferred disclosed embodiment employs a flow rate of roughly 10 to 40 gallons per minute, and more preferably around 25 gallons per minute, with an upper and lower surface area within each chamber of approximately 72 in$^2$.

A preferred embodiment of the system 10 comprises an outer housing 40 made from a non-conductive material, such as a plastic or another polymer. Opposite electrodes 12 and 14 each comprise a substantially flat metal sheet positioned within the housing 40 sealed along all edges of the respective electrodes either to a portion of the housing or an intermediate member like a gasket. In a preferred embodiment, the metal sheets are stainless steel and take a rectangular shape of equal dimensions. The stainless steel sheet electrodes 12 and 14 are spaced from one another substantially parallel approximately 0.1875 inches apart. A substantially flat porous divider 16, preferably in the form of a sheet of an alumina material, is positioned approximately equidistant between the spaced metal sheets 12 and 14. Preferably, the porous divider 16 is also sealed within the housing 40 at all edges, thereby defining a first chamber 18 with the first electrode 12 and a second chamber 20 with the second electrode 14. The spacing distance between the respective electrodes 12 and 14 and the porous divider 16 can vary as needed for specific operating conditions of the system 10, such conditions including fluid flow rate, voltage applied to the electrodes, initial ORP of the incoming fluid and desired ORP of the output modified fluid. Embodiments exist with spacing between an electrode (12 or 14) and the porous divider of up to 0.2 inches, and even more preferably between approximately 0.025 and 0.125 inches. A particularly preferred embodiment includes spacing of approximately 0.0625 inches between each electrode (12, 14) and the divider 16. In a preferred embodiment, each of the electrodes 12 and 14, and the porous divider are each approximately 0.0625 inches thick. These dimensions are only exemplary, and non-limiting to the scope of the disclosure. Further, embodiments exist wherein the first electrode 12 and second electrode 14 are not equidistant from the porous divider 16.

The housing 40 may take the form of a four-sided plastic cap for accommodating rectangular metal sheets 12 and 14, and the porous divider 16 with each side of the plastic cap 40 mating with each of the metal sheets and the divider in a fluid tight seal. The plastic cap housing 40 typically includes one or more fluid ports in an end cap 26 in communication with the incoming fluid flow path, defining an inlet to each of the first and second treatment chambers, 18 and 20. Each of the electrodes is electrically connected to a separate electric current with opposite electrical charges to the electrodes. Non-conductive sealing members, such as gaskets, may be included at the interface between the housing 40 and each of the conductive members 12 and 14, and the divider 16, to assist in maintaining a fluid tight seal.

In the disclosed system 10, the conductive dividers, 12 and 14, form the oppositely charged electrodes (i.e., become an anode or cathode) when a positive or negative electrical charge is applied during operation of the system. For example, in a preferred embodiment, a voltage of varying strength up to 180V DC with a current between approximately 30-40 amperes is provided between electrode 12 and 14. One skilled in the art of oxygenating fluid treatment can appreciate that actual operating conditions that are linked with properties of the fluids, such as for example the total dissolved solids (TDS), will vary. Necessarily, more power in voltage and amperage is required to treat fluids with higher TDS measurements.

As shown and described, the porous divider 16 is positioned intermediate a respective outer conductive member 12 and inner conductive member 14, thereby defining adjacent flow chambers 18 and 20. Preferably, the porous divider is formed from a ceramic or alumina material. In the depictions of the Figures, the first chamber 18 is designated as the "positive" chamber and second chamber 20 is designated as the "negative" chamber, as a result of conductive member 12 acting as the cathode and conductive member 14 acting as the anode. As the separate streams of fluid flow through the respective chambers, 18 and 20, ions are created and separated between the respective chambers by the porous divider 16. The porous divider 16 is preferably an aluminum oxide divider with a minimum surface area over which fluid passes of approximately 72 in$^2$ (sheets of 6 in×12 in dimensions), positioned approximately equidistant between the cathode 12 and the anode 14, thereby providing substantially equal volumes of fluid flow through the respective chambers, 18 and 20. This is of course an exemplary preferred surface area, chosen for a particular flow rate (25 gallons per minute), and non-limiting to the herein disclosure.

Whether elevated (positive) ORP fluid or reduced (negative) ORP fluid is formed in one chamber or the other chamber (18 or 20) is simply a matter of operation choice, dependent on the relative orientation of the electrodes (12 and 14). The porous divider 16 preferably includes series of 0.05 micron diffusion paths sized to allow ionic movement/transfer between the respective electrodes, while inhibiting molecular diffusion. Preferably, the porosity of the aluminum oxide divider is within the range of approximately 30% to approximately 60%.

Further, fluid flow rate through each chamber can be altered by varying the size of the openings leading to the particular chamber. With reference to FIG. 3, a side view of a portion of the endcap 26 of the housing 40 is shown. Larger slots 28 are formed in the housing in a position aligned with the positively charged chamber 18, while smaller openings 30 are formed in the housing in a position aligned with the negatively charged chamber 20. This comparative sizing necessarily results in a faster flow rate through the positive chamber than through the negative chamber.

The exemplary embodiment described herein comprises rectangular metal sheets (12 and 14), divider 16 and housing 40. It should be understood that these elements can be formed in a variety of shapes and sizes, scaled as desired for a particular application, performance and fluid flow. For example, the disclosed refraction technology oxygen modification system 10 may include conductive members 12 and 14 and/or porous divider(s) 16 having general cross sectional shape of, for example, a parallelogram, arc, inverted arcs, or ellipses or different contours, such as toothed, splined, waved or spurred. As noted above, a preferred embodiment includes conductive members 12 and 14, and porous dividers 16 each having dimensions of approximately 12 inches×6 inches, resulting in a surface area of each element interfacing flowing fluid of 72 in$^2$ (approximately 465 cm$^2$). This exemplary sizing can be scaled upward to accommodate and treat larger volumes of fluid.

Further, the fluid flow rate may be controlled in a plurality of different ways. In addition to the end cap 26 depicted in FIG. 3, a variable on/off valve (not depicted) positioned along the incoming fluid flow line 31 upstream of the end cap 26 can be used to assist regulation of the volume of incoming fluid flow. An outlet valve (not depicted) may also be positioned along each of the outgoing fluid flow lines 32a and 34a upstream of the respective outlet 32 and 34 to control the rate of flow through each respective positive and negative chamber 18 and 20. Regulation of flow with the inlet and outlet valves in this manner allows manipulation to desired ORP values by maintaining the fluid being treated within each chamber for either longer or shorter durations. For example, slowing fluid flow through a positive chamber 18, thereby maintaining fluid within the chamber for a longer duration, results in output fluid from that chamber having a higher positive ORP value than fluid passing through at a faster flow rate under the same conditions.

As depicted in FIG. 1, the refraction technology oxygen modification system 10 may optionally include an ultraviolet (UV) light source 38 exposed to incoming fluid flow. The preferred embodiment of the ultra violet light source 38 is within a glass enclosure that allows outward transmission of UV rays positioned such that all incoming fluid is exposed to UV rays prior to entering the positive and negative treatment chambers 18 and 20. The depicted positioning ensures that all fluid subject to ORP modification in the system 10 is treated with UV radiation. Exposing the incoming fluid to UV radiation kills pathogens that may be present in the incoming fluid prior to modification of monoatomic oxygen levels. While raising the ORP of the incoming fluid to certain positive levels will necessarily kill pathogens that may be present, pathogens entering the negative chamber would not be killed by negative modification. The UV light source therefore allows the system to provide both positive and negative ORP that are substantially pure.

FIG. 1 also shows a plurality of adjustment fasteners 42 extending the length of the system 10. The depicted fasteners 42 are in the form of elongate screws through opposite sides of the housing 40. The fasteners 42 are tightened via a threaded bolt or similar to lock the sheet-like inner members (electrodes 12 and 14, and porous divider 14) rigidly in place. The fasteners 42 can optionally be loosened to release the housing and allow access to the inner portions of the system 10, for removal of the inner members for inspection, cleaning or, if necessary, repair and replacement. Typically, at least one side of the housing 40 may be removable or pivotable relative to an adjacent side to allow the sheet electrodes 12 and 14, and divider 16 to be slid out from the housing when the fasteners 42 are removed (left to right sliding in the representative depiction of FIG. 1). Preferably, the system 10 includes four or more fasteners 42 in total—at least two upper fasteners spaced from one another above the first electrode 12, and at least two lower fasteners spaced from one another below the UV source 38 in the FIG. 1 depiction.

Figure 2:
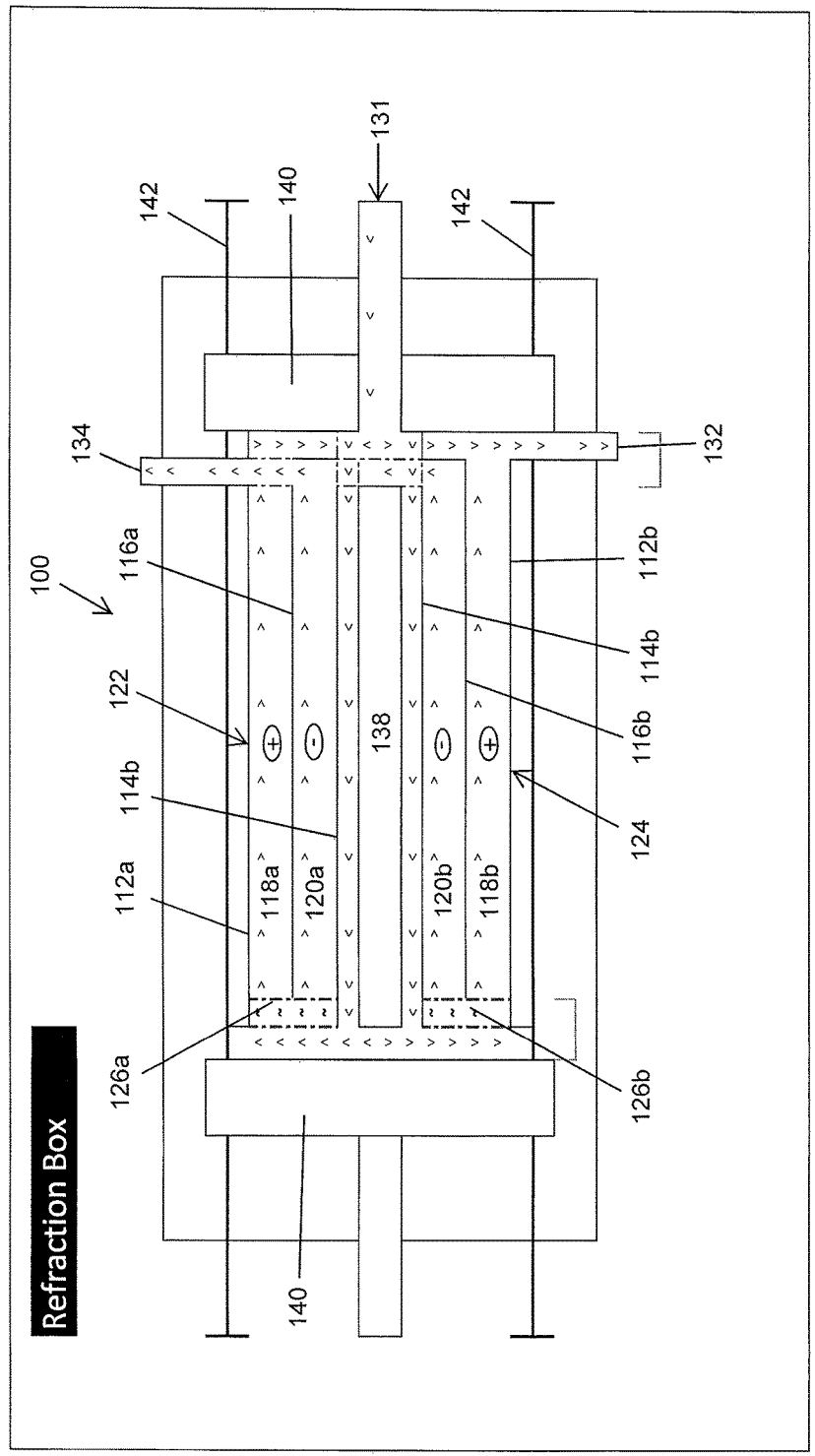
FIG. 2 shows another embodiment of the disclosed refraction oxygen modification system.

FIG. 2 depicts an alternate embodiment of the disclosed refraction technology oxygen modification system 100. This embodiment of the system 100, includes an upper treatment section 122 and a lower treatment section 124, each having a positive modification chamber (118a and 118b) and a negative ORP modification chamber (120a and 120b). Each of the treatment sections 122 and 124 is configured and operates substantially like the system 10 of FIG. 1. That is, each section 122 and 124 has a first electrode (112a and 112b) spaced from a second electrode (114a and 114b) with a porous divider (116a and 116b) positioned therebetween. A single source of incoming fluid at an initial ORP enters via the inlet 131 and is split between the upper and lower sections 122 and 124. Each treatment section includes an end cap (126a and 126b) like that shown as reference numeral 26 in FIG. 3 for providing incoming fluid to its positive ORP modification chamber 118a and 118b, and its negative ORP modification chamber 120a and 120b. Further, as shown in FIG. 3, the outgoing fluid lines of the positive chambers 118a and 118b may be combined upstream of a single positive ORP modified fluid outlet 132. Likewise, the negative ORP modified fluid lines may join upstream of a single negative ORP fluid outlet 134. Like the embodiment of the system 10 of FIG. 1, the system 100 has an outer housing 140 made from a non-conductive material that maintains the electrodes and dividers in a fluid tight seal around all edges.

In the depicted embodiment, a positive charge is provided to the first electrodes 112a and 112b (also referred to as the outer electrodes), and a negative charge is provided to the second (inner) electrodes 114a and 114b. The respective first electrodes may be electrically connected to one another, and the second electrodes may be electrically connected to one another, for providing the same voltage to each cathode and anode from a singular positive and negative source. Alternatively, respective first electrodes and respective second electrodes can be electrically insulated from one another, allowing a different voltage to be provided to each electrode and greater variation to the system. Like with the single-treatment section embodiment of FIG. 1, which electrode acts as an anode and cathode is a matter of operation choice simply dependent on which electrode(s) receive positive and negative voltage.

The preferred operating conditions, dimensions, spacing, materials, relative relationships and positioning of each of the electrodes and porous divider are substantially the same as in the embodiment of FIG. 1. The dual-section system 100 of FIG. 2 is simply capable of processing a larger volume of fluid per unit time relative to the system 10 shown in FIG. 1.

As shown in FIG. 3, a UV chamber 138 may be positioned centrally so that all fluid entering the system 100 is exposed to UV radiation prior to ORP modification. Like the system 10 of FIG. 1, the dual-section system 100 of FIG. 2 can include a plurality of adjustment fasteners 142 extending longitudinally through opposite sides of the housing 140.

Positive ORP output fluid and negative ORP fluid produced by the disclosed systems 10 and 100 can be used for a wide variety of useful purposes. Positive ORP fluid has shown to provide strong pathogen killing properties without the safety drawbacks of chemical-based ORP modification techniques. Negative ORP fluid has been shown to provide positive physiological effects when consumed by individuals. Further, the modified fluids produced by the herein described system and method have shown resistance to normalization toward neutral ORP levels as compared to chemical-based ORP modified fluids.

Examples 1 and 2 below show the strong pathogen killing properties and industrial impact of positive ORP fluid produced by the described system and method.

Example 1

In Example 1, suspensions of *Pseudomonas aeruginosa* (Sample A), *Salmonella* sp (Sample B), *Listeria monocytogenes* (Sample C), *Staphylococcus aureus* (Sample D), *Escherichia coli* (Sample E) and *Serratia marcescens* (Sample F) were prepared and diluted to 100,000 fu/mL for inoculation. The level of each 6 inoculum suspension was tested by plating a dilution of the suspension containing 100 cfu/mL.

For each bacteria suspension (A-F), three 100 mL samples were prepared for comparative purposes. Each 100 mL sample was inoculated with 100,000 colony forming units (cfu) of the appropriate bacteria, resulting in 1,000 cfu of bacteria per mL of sample.

Each sample was then mixed with modified fluid prepared using the disclosed system 10 and method with an ORP value of approximately +700. The samples of each bacteria were tested at different intervals from the time of mixing with modified fluid: 1 mL of each sample was removed at 30 seconds, 2 minutes, 5 minutes and 10 minutes measured from the time of mixing. Each 1 mL portion was then mixed by swirling with Tryptic Soy Agar (TSA) immediately after removal.

The 1 mL portions of Sample B (*Salmonella*), Sample D (*Staphylococcus*) and Sample E (*Escherichia*) were incubated at 38° C. The 1 mL portions of Sample A (*Pseudomonas*), Sample C (*Listeria*) and Sample F (*Serratia*) were incubated at 32° C. After 48 hours of incubation the plates were inspected for presence of bacteria colonies.

The results showed that fluid samples of +700 ORP fluid (from the negative charge output 34) successfully eliminating each of the six tested bacteria within 30 seconds of the bacteria's addition.

Example 2

FIG. 4 shows a photo time table depicting a test screen cleaning using the modified fluid treated with the disclosed oxidation refraction system 10. Fluid samples from the negative chamber (+700 ORP) were tested and displayed varying degrees of effectiveness.

Figure 4E:
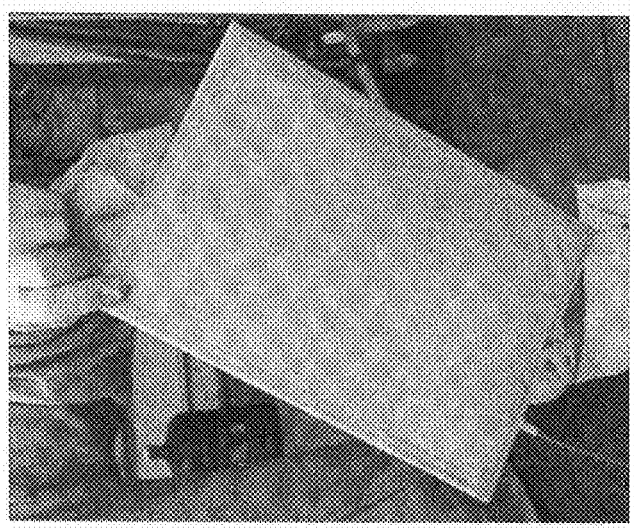
Figure 4D:
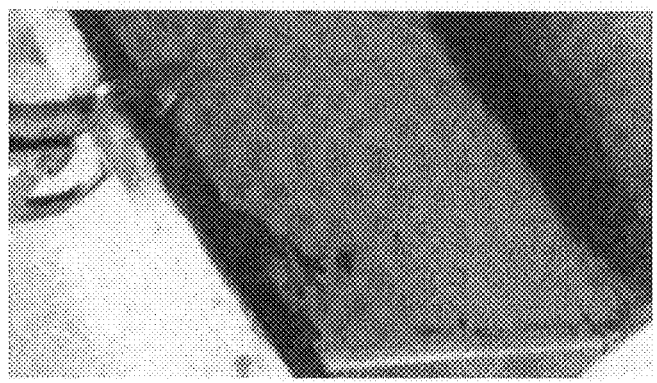
Figure 4C:

FIG. 4A depicts the fully contaminated and dried filtration screen to be treated. FIG. 4B depicts the screen of FIG. 4A approximately 5 seconds after an initial rinse with the oxidized fluid. FIG. 4C depicts the screen 15 seconds after the initial rinse with oxidized fluid. FIG. 4D depicts the screen 20 seconds after the initial rinse. FIG. 4E depicts a fully cleaned screen, less than 30 seconds after the initial rinse with oxygen modified fluid. FIG. 4E further shows that the fluid draining from the filter is clear in appearance (clean).

The actual experimental photos shown in FIGS. 4A-4E and described above are an example of a test performed to eliminate the buildup and bacteria on a filtration screen used for filtering hard waste at a sewage treatment plant. The known procedure for cleaning the same filtration screens is a chemical treatment, whereby highly concentrated chlorine or acids are forced through the screen material over a course of several hours. A typical treatment with concentrated acid takes up to four hours, thereby requiring a significant duration of shutdown at the facility. Moreover, such chemical cleansing treatments require special handling and disposal of the toxic treatment chemicals. The force feeding process also causes damage to the screens over time.

In contrast, the oxygen modified fluid with an ORP value of +700 produced by the disclosed refraction system 10 eliminates the use of chemical cleansing techniques and force feeding of fluid through screens, thereby significantly extending the life of each screen in a safe, non-toxic environment in approximately 30 seconds, thereby eliminating hours of downtime at the sewage treatment plant.

The refraction technology oxygen modification system 10 allows variations to control the output to a desired ORP fluid, as desired for a specific application. Therefore it concluded that the modified water output for the specific ORP fluid selected (+700 ORP fluid) was extremely effective in elimination of the bacteria, loosening the grip of the attached/clogged materials captured on the test screens and effectively removing these materials from the screens. As shown and described in FIG. 4, no chemicals were used under this controlled test conditions.

Although the inventive refraction technology oxygen modification system and process has been described in detail, those skilled in the art will understand that various changes, substitutions, and alterations may be made without departing from the spirit and scope of the invention in its broadest form. The system is not limited to the preferred embodiment described herein. For example, the device may be scaled in size and shape to vary from application to application, depending upon the flow and ORP requirements as well as batch sample applications.

The invention claimed is:

1. A method for modifying the monoatomic oxygen level in a fluid, comprising:
   (a) providing a first electrode defining a first conductive surface spaced from a second electrode defining a second conductive surface;
   (b) providing a porous divider positioned intermediate the first electrode and second electrode and defining a first fluid treatment chamber with the first conductive surface and a second fluid treatment chamber with the second conductive surface;
   (c) providing a positive charge to the first electrode and a negative charge to the second electrode;
   (d) flowing an initial fluid having an initial oxidation reduction potential (ORP) value from an inlet to the first chamber and the second chamber via an end cap defining a first fluid inlet to the first chamber and a second fluid inlet to the second chamber, wherein the first fluid inlet is configured to allow a greater volume of fluid per unit time to the first chamber than the second fluid inlet allows to the second chamber, thereby modifying the monoatomic oxygen level of the initial fluid in both chambers; and
   (e) collecting positive oxygen fluid having a positive ORP value greater than the initial ORP value from the first chamber and negative oxygen fluid having a negative ORP value lower than the initial ORP value from the second chamber.

2. The method of claim 1, wherein the first and second electrodes are substantially flat sheets positioned substantially parallel to one another other.

3. The method of claim 1, wherein fluid flows at a first rate $F_1$ through the first chamber and fluid flows through the second chamber at a second rate $F_2$ that is slower than the first rate.

4. The method of claim 1, comprising allowing the incoming fluid to remain in the first chamber until the positive ORP value is increased to at least twice the initial ORP value.

5. The method of claim 4, comprising allowing the incoming fluid to remain in the first chamber until the positive ORP value is increased to at least 600 mV.

6. The method of claim 1, comprising allowing the incoming fluid to remain in the second chamber until the negative ORP value is reduced to a negative ORP value.

7. The method of claim 6, comprising allowing the incoming fluid to remain in the second chamber until the negative ORP value is reduced to at least −300 mV.

8. The method of claim 1, comprising providing a charge between the anode and the cathode within a range of approximately 50 volts to approximately 150 volts.

9. A method of killing a pathogen, comprising the steps of:
   (a) providing an initial fluid having an initial oxidation reduction potential (ORP) value;
   (b) increasing the ORP of a portion of the initial fluid without introducing a chemical to yield a natural positive ORP fluid; and
   (c) contacting a pathogen with at least a portion of the natural positive ORP fluid, wherein step (b) comprises the substeps of:
   (i) splitting the initial fluid into a first portion and a second portion;
   (ii) flowing the first portion through a first chamber defined by a first electrode spaced from a porous divider to yield the positive ORP fluid;
   (iii) flowing the second portion through a second chamber defined by a second electrode spaced from the porous divider, the second electrode in electrical communication with the first electrode to yield a negative ORP fluid with a ORP value below the initial ORP value; and (iv) collecting the positive ORP fluid, wherein
in step (i), the initial fluid is split via an end cap defining a first fluid inlet to the first chamber and a second fluid inlet to the second chamber, wherein the first fluid inlet is configured to allow a greater volume of fluid per unit time to the first chamber than the second fluid inlet allows to the second chamber, and
an electrical charge is provided between the first electrode and second electrode during substeps (ii) and (iii).

10. The method of claim 9, wherein the ORP value of the positive ORP fluid deviates from the initial ORP more than the value of the positive ORP fluid deviates from the initial ORP.

11. The method of claim 9, comprising the steps of:
(d) allowing the ORP value of excess natural positive ORP fluid to reduce toward the initial ORP to yield a reduced positive ORP fluid, and
(e) recovering the reduced positive ORP fluid.

12. The method of claim 9, wherein the natural positive ORP fluid has an ORP value of at least +400.

13. The method of claim 12, wherein the natural positive ORP fluid is between approximately +500 and approximately +1300.

14. The method of claim 9, wherein the pathogen is present on a substrate, comprising the step of dipping the substrate and pathogen into a volume of natural positive ORP fluid.

15. The method of claim 14, wherein the substrate is a filter used in a sewage treatment system.

16. An oxygen modification system, comprising:
a first electrode defining a first flow surface;
a second electrode spaced from the first electrode and defining a second flow surface;
a porous divider positioned intermediate and spaced from each of the first and second electrodes, thereby defining a first flow chamber with the first electrode and a second flow chamber with the second electrode, the first flow chamber having a first chamber inlet and first chamber outlet and the second flow chamber having a second chamber inlet and a second chamber outlet; and
an end cap defining a first fluid inlet to the first chamber and a second fluid inlet to the second chamber, wherein the first fluid inlet is configured to allow a greater volume of fluid per unit time to the first chamber than the second fluid inlet allows to the second chamber, wherein
a positive electrical charge is applied to the first electrode and a negative electrical charge is applied to the second electrode and a fluid having an initial oxygen reduction potential (ORP) value flows through the first chamber and through the second chamber, yielding a positive oxygen modified fluid from the first chamber outlet having a first ORP value above the initial ORP value and a negative oxygen modified fluid from the second chamber outlet having a second ORP value below the initial ORP value.

17. The oxygen modification system of claim 16, wherein the first and second electrodes are flat sheets of metal and the porous divider is a flat sheet of an alumina material.

18. The oxygen modification system of claim 17, wherein the first and second electrodes and porous divider each defines a plane and the planes are positioned substantially parallel to one another.

* * * * *